US005656462A

United States Patent [19]
Keller et al.

[11] Patent Number: 5,656,462
[45] Date of Patent: Aug. 12, 1997

[54] METHOD FOR SYNTHESIZING CDNA USING A POLYNUCLEOTIDE IMMOBILIZED SUPPORT

[75] Inventors: Cylia Keller, El Toro; Masato Mitsuhashi; Tatsuo Akitaya, both of Irvine, all of Calif.

[73] Assignees: Hitachi Chemical Co., Ltd., Tokyo, Japan; Hitachi Chemical Research Center, Inc., Irvine, Calif.

[21] Appl. No.: 287,075

[22] Filed: Aug. 8, 1994

Related U.S. Application Data

[63] Continuation of Ser. No. 827,975, Jan. 29, 1992, abandoned.
[51] Int. Cl.$^6$ .............................. C12P 19/34; C12Q 1/68; C12N 15/00; C12N 15/09
[52] U.S. Cl. ..................... 435/91.2; 435/6; 435/91.51; 435/172.1; 536/23.1
[58] Field of Search .............................. 435/91.1, 172.3, 435/6, 91.2, 91.5, 91.51, 91.52, 91.53, 172.1; 536/23.1

[56] References Cited

U.S. PATENT DOCUMENTS

| | | | |
|---|---|---|---|
| 4,734,363 | 3/1988 | Dattagupta et al. | 435/91.1 |
| 4,751,177 | 6/1988 | Stabinsky | 435/6 |
| 4,797,355 | 1/1989 | Stabinsky | 435/6 |
| 4,894,325 | 1/1990 | Englehardt et al. | 435/6 |
| 4,978,724 | 12/1990 | Clark | 525/350 |
| 5,082,935 | 1/1992 | Cruickshank | 536/23.1 |

FOREIGN PATENT DOCUMENTS

| | | |
|---|---|---|
| 0152886 | 8/1985 | European Pat. Off. . |
| 0329822 | 8/1989 | European Pat. Off. . |
| 0369775 | 11/1989 | European Pat. Off. . |
| 0370694 | 11/1989 | European Pat. Off. . |
| 0397269 | 5/1990 | European Pat. Off. . |
| 0422872 | 10/1990 | European Pat. Off. . |
| 3-147800 | 6/1991 | European Pat. Off. . |
| 0469610 | 8/1991 | European Pat. Off. . |
| 8603782 | 7/1986 | WIPO . |
| 8801302 | 2/1988 | WIPO . |
| 9006044 | 6/1990 | WIPO . |
| 9006043 | 6/1990 | WIPO . |
| 9006045 | 6/1990 | WIPO . |
| 9006042 | 6/1990 | WIPO . |
| 9107505 | 5/1991 | WIPO . |

OTHER PUBLICATIONS

Raineri et al "Improved Efficiency for Single–Sided PCR . . . " Nucleic Acids Research 19 (1991), 4010.
1992 Gibco BRL Catalogue and Reference Guide, copyright 1991, Life Technologies, Inc. p. 432.
Sambrook et al, Molecular Cloning, A Laboratory Manual, Second Edition, Cold Spring Harbor Laboratory Press, 1989, pp. 9.38–9.40.
Palazzolo et al. Gene vol. 52, 1987, pp. 197–206.
Inouye et al. J. Clin. Microbiol. (1990) vol. 28 (6) :1469–1472.

A. Swaroop et al., "Differential expression of novel $G_{s\alpha}$ signal transduction protein cDNA species". Nucleic Acids Research, vol. 19, No. 17, 1991, pp. 4725–4729.
Polsky–Cynkin et al., "Use of DNA Immobilized on Plastic and Agarose Supports to Detect DNA by Sandwich Hybridization", Clinical Chemistry, vol. 31, No. 9, 1985, pp. 1438–1443.
Saiki et al., "Primer–Directed Enzymatic Amplification of DNA with a Thermostable DNA Polymerase", Science, vol. 239, 29 Jan. 1988, pp. 487–491.
R. Bischoff et al., "Introduction of 5'–Terminal Functional Groups into Synthetic Oligonucleotides for Selective Immobilization", Analytical Biochemistry, vol. 164, No. 2, 01 Aug. 1987, pp. 336–344.
J. Rey–Campos et al., "Synthesis of Thymosin $\alpha_1$ Precursor cDNA and Purification of Active mRNA by Affinity Chromatography", International Journal of Biochemistry, vol. 15, 1983, pp. 155–157.
T. Atkinson et al., "A convenient procedure for the synthesis of oligodeoxyribonucleotide affinty columns for the isolation of mRNA", Nucleic Acids Research, vol. 16, No. 13, 1988, p. 6232.
J. A. Arias et al., "Promoter–dependent Transcription by RNA Polymerase II Using Immobilized Enzyme Complexes", Journal of Biological Chemistry, vol. 264, No. 6, 1989, pp. 3223–3229.
C. R. Thrash et al., "Synthesis of RNA from Cellulose–bound Complementary DNA", Journal of Biological Chemistry, vol. 252, No. 16, 1977, pp. 5615–5618.
Bethesda Research Laboratories Life Technologies, Inc. Product: Vanadyl Ribonucleoxide Complex.
Pal Venetianer, et al., Pro Nat. Acad. Sci. USA, V1.71, No.10,pp. 3892–3895, Oct. 1974; "Enzymatic Synthesis of Solid Phase–Bound DNA Sequences Corresponding to Specific Mammalian Gene".
P.T. Gilham, Journal of the American Chemical Society, vol.86, pp.4982–4985; "The Synthesis of Polynucleotide–Celluloses and Their use in the Fractionation of Polynucleotides". (1964).

(List continued on next page.)

Primary Examiner—John L. LeGuyader
Assistant Examiner—Thomas G. Larson
Attorney, Agent, or Firm—Knobbe Martens Olson & Bear

[57] ABSTRACT

The present invention provides a nucleotide-immobilized support which includes an insoluble support and a polynucleotide bound to the support. This polynucleotide includes at least one sequence complementary to a polyadenylic acid tail of a mRNA. The nucleotide-immobilized support is useful for a variety of methods, including the synthesis of both sense and antisense cDNA, as well as double stranded cDNA. The nucleotide-immobilized support is also useful for synthesis of both sense and antisense mRNA. Additionally, the nucleotide-immobilized support also provides an improved method of placing a cDNA sequence into a vector in a particular orientation. The present invention also includes a new method for binding polynucleotides to insoluble supports.

4 Claims, 3 Drawing Sheets

OTHER PUBLICATIONS

M.R. Ven Murthy, et al., Nucleic Acids Research, vol. 14, No. 17, Jul. 24, 1986; "Preparation and Biochemical Manipulation of mRNAs and CDNAs on small Oligo(dt)–cellulose discs".

Jane A. Matthews, et al., Analytical Biochemistry 169, pp.1–25 (1988); "Analytical Strategies for the Use of DNA Probes".

Stefan Stamm, et al., Nucleic Acids Research, vol.19, No.16, p. 1350; "Sanchored PCR: PCR with cDNA Coupled to a Solid Phase". (1991).

R. Julian S. Duncan, et al., Analytical Biochemistry 132, pp.68–73 (1983); "A New Regent Which May Be Used to Introduce Sulfhydryl Groups into Proteins, and Its Us in the Preparation of Conjugates for Immunoassay".

Seiichi Hashida, et al., Journal of Applied Biochemistry 6, pp.56–63 (1984); "More Useful Maleimide Compounds for the Conjugation of Fab' to Horseradish Peroxidase through Thiol Groups in the Hinge".

Hidenori Yamada, et al., Biochemistry 1981, 20 pp.4836–4842; "Selective Modification of Aspartic Acid–101 in Lysozyme by Carbodiimide Reaction".

James V. Staros, et al., Analytical Biochemistry 156, pp.220–222(1986); "Enhancement by N–Hydroxsulfosuccinimide of Water–Soluble Carbodiimide–Mediated Coupling reactions".

Norman Arnheim, et al., C&EN, Oct. 1, 1990, pp. 36–46; "Polymerase Chain Reaction".

"Basic Methods in Molecular Biology" by Davis et al., p. 77.

SATA: Succinimidyl-S-acetylthioacetate
Sulfo-SMCC: Sulfosuccinimidyl-4-(N-maleimidomethyl) cyclohexane-1-carboxylate EDC: 1-ethyl-3-(3-dimethylaminopropyl) carbodiimide hydrochloride
Sulfo-NHS: N-hydroxysulfosuccinimide

METHOD FOR SYNTHESIZING CDNA USING A POLYNUCLEOTIDE IMMOBILIZED SUPPORT

This application is a continuation of application Ser. No. 07/827,975, filed Jan. 29, 1992, now abandoned.

BACKGROUND OF THE INVENTION

In most living organisms, genetic information is stored in the form of DNA. This DNA is transcribed into messenger RNA (mRNA) which then is translated into protein. In eukaryocytes, there is usually some loss of genetic information in the process of converting genomic DNA to the mature mRNA. This loss can be due to introns/exons, RNA splicing, or protein processing. Therefore, the genetic basis of protein structure is more advantageously studied using mRNA than genomic DNA.

Unfortunately, mRNA is extremely unstable and easily digested by various ribonuclease (RNA digesting) enzymes (hereafter referred to collectively as "RNase") making experimentation difficult. Thus, many researchers have chosen to study DNA copies (cDNA) of interesting mRNA molecules. These copies are made using the enzyme reverse transcriptase (RT), isolated from retrovirus', which produces a single stranded DNA copy of the target mRNA.

Double stranded DNA (ds-cDNA) is generally more stable than single stranded cDNA (hereafter called "ss-cDNA"). The method of converting ss-DNA to ds-DNA using the enzyme DNA polymerase is well known in the art. The genetic information stored on ds-cDNA can then be used in various protocols, for example inserting ds-cDNA into expression vectors, which are then introduced into various cells. Promoters and restriction sites located on these vectors can then be used as tools for studying transcription and translation of the ds-cDNA.

In addition to using vector based promoters for transcription of mRNA nucleotides containing the polypeptide coding sequence (sense mRNA), antisense mRNA transcribed from the complementary cDNA strand can also be produced. Antisense mRNA is a useful tool for understanding biological function of a protein or mRNA whose function is unknown. Antisense RNA molecules are used to block production of specific proteins by annealing to the target mRNA and inhibiting translation. Therefore, it is anticipated that this type of translational inhibition will be important in the study of various gene products associated with a variety of diseases states.

Besides being a used for DNA polymerase based catalysis of ds-cDNA synthesis, ss-cDNA can be used as a template for polymerase chain reaction (hereafter called "PCR"). This method allows the rapid reproduction and enhancement of a specific gene sequence through the use of opposing nucleotide primers and a heat stable DNA polymerase. Multiple cycles of annealing and DNA synthesis rapidly produces many copies of the targeted gene. Thus, sense ss-cDNA can be used to specifically amplify a segment of its corresponding ds-cDNA.

One currently known protocol for producing ds-cDNA is the liquid phase method described in Sambrook, et al., "Molecular Cloning, A Laboratory Manual, 2d Ed.," Cold Spring Harbor Press, Cold Spring Harbor, N.Y. (1989) (hereinafter referred to as "Molecular Cloning"). The complete disclosure of this manual is incorporated herein by reference thereto. In the liquid phase method, antisense ss-cDNA is produced from mRNA using reverse transcriptase, followed by mRNA digestion with RNase. Ds-cDNA is then synthesized from complementary chains of the remaining antisense ss-cDNA using DNA polymerase. DNA polymerase reactions following reverse transcriptase don't require a specific primer since the RT leaves synthesized ss-cDNA with a self-priming loop structure at the 3' end.

With the liquid phase method, the resulting ds-cDNA does not contain a marker to identify the molecule's orientation. Accordingly, the newly synthesized ds-cDNA cannot be readily inserted into a cloning vector since 50% of the clones will be in the wrong orientation for transcription. A rapid method of directionally cloning mRNA into a vector would therefore be desirable.

Ss-cDNA or ds-cDNA can also be produced using solid phase material. (I. Raineri et al. in *Nucleic Acids Research*, 19:4010 (1991)). In the solid phase method, polydeoxythymidylic acid (poly dT), usually immobilized onto porous beads, is hybridized to the polyadenlic acid (poly A) tail of mRNA. Then, antisense ss-cDNA is synthesized from the bound polyadenelated mRNA by reverse transcriptase. After the template RNA is digested, second strand cDNA is synthesized by DNA polymerase. The resultant ds-cDNA has its antisense strand immobilized to the beads.

The solid phase method, however, yields product that cannot be disassociated from the insoluble support. In order circumvent this problem, the ss-cDNA can be released from the support-immobilized ds-cDNA by heating, and thereafter used to synthesize ds-cDNA using PCR. However, this adds another step to the reaction and requires an appropriate set of primers for every PCR reaction.

There is therefore a need for a simple method of creating unbound ds-cDNA clones from isolated mRNA. This method should preferably result in unbound, directionally cloneable products.

There are also various methods known of synthesizing mRNA from cDNA clones, one example is the liquid phase method which was described by S. Shichijo, et al. in *Journal of Neuroscience Research*, 30:316–320 (1991). In this method, ds-cDNA is inserted into a vector containing a RNA promoter. The vector is then linearized by restriction enzyme digestion and mRNA is synthesized using RNA polymerase. The synthesized mRNA is then treated with a deoxyribonuclease (DNA digesting) enzyme (hereafter called "DNase") to remove the template DNA. If necessary, a polyadenelated tail can be added to the end of the newly synthesized RNA using the enzyme Terminal Transferase and dATP's.

The solid phase method of producing mRNA is also well known. Hironori Terada, et al., "Movement analysis of transcription by immobilized DNA," *Biophysics* 31:49–52 (1991) describe one such method. In this method, a DNA sequence is digested from the genome of bacteriophage λ by restriction enzyme cleavage, resulting in random DNA fragments with "sticky ends. T4 DNA polymerase is then used to fill in these sticky ends using biotinylated dUTP. The restriction enzyme is selected so as to leave a sticky end with an exposed dA nucleotide to which the biotinylated dUTP will hybridize during synthesis of DNA by the T4 DNA polymerase. Random sequences are then immobilized to an acrylamide support bearing avidin. mRNA can then be synthesized from those sequences bearing a natural λ promoter sequence using a polymerase T7 RNA polymerase or SP6 RNA polymerase. This system was designed to study the kinetic analysis of transcription in bacteriophage λ.

Both the liquid phase and solid phase methods of mRNA synthesis have disadvantages. The liquid phase method requires the use of a vector containing a RNA promoter, and also requires that the vector be converted into a linear sequence after insertion. The solid phase method does not always provide complete genetic information because the source of this information is immobilized genomic DNA and not mRNA. Thus, improved methods of mRNA synthesis would be desirable.

Stamm et al. in *Nucleic Acids Research*, 19:1350 (1991) described oligonucleotides covalently coupled via an amino link to a solid support for use in facilitating PCR experiments. However, the technique described by Stamm et al. does not specifically provide for the production of cDNA or RNA. Moreover, no mechanism is provided for removing the oligonucleotides covalenty coupled to the support.

SUMMARY OF THE INVENTION

This invention is related to a polynucleotide immobilized support which is useful in the preservation and analysis of genes, the preservation method of genes using polynucleotide-immobilized support, and methods of synthesizing single stranded sense complementary DNA (hereafter called "cDNA"), double stranded cDNA (hereafter called "ds-cDNA"), sense messenger RNA ("mRNA") and of antisense mRNA.

One aspect of the present invention provides a nucleotide-immobilized support which includes an insoluble support and a polynucleotide bound to the support. This polynucleotide includes at least one sequence complementary to a polyadenylic acid tail of a mRNA. The nucleotide-immobilized support is useful for a variety of methods, including the synthesis of both sense and antisense cDNA, as well as double stranded cDNA. The nucleotide-mobilized support is also useful for synthesis of both sense and antisense mRNA. Additionally, the nucleotide-immobilized support provides an improved method of directionally placing a cDNA sequence into a vector. The present invention also includes new methods for binding polynucleotides to insoluble supports.

The invention focuses on a polynucleotide containing a sequence complementary to a polyadenylic acid tail of a mRNA, such as oligo (dT). In certain preferred aspects of the present invention, this polynucleotide can also contain recognition sites for restriction enzymes and RNA promoter sequences. The polynucleotide is generally immobilized on an Insoluble Dish such as microtiter plates. The present invention polynucleotide-immobilized support can be used to synthesize full length ds-cDNA, sense ss-cDNA, and antisense mRNA. Furthermore, the immobilized ss-cDNA is stable for a long enough time to perform repeated rounds of ds-cDNA or mRNA synthesis.

One embodiment of the current invention is a nucleotide-immobilized support made of an Insoluble Dish (ID), which is preferably a microtiter plate, with a polynucleotide bound to the dish. The bound polynucleotide contains at least one sequence complementary to the polyadenylic acid tail of mRNA, for example poly(dt). In certain preferred embodiments, this polynucleotide also contains, at least one restriction enzyme site. In an even more preferred embodiment, this polynucleotide has an RNA promoter site in addition to the restriction enzyme site. An alternative embodiment of the present invention is a nucleotide-mobilized support, preferably with a polynucleotide bound to an insoluble support containing at least one RNA promoter. The most preferable embodiment contains either the T7 or SP6 RNA promoter.

A further embodiment of the current invention is a nucleotide-immobilized support, made of an insoluble support, and a bound polynucleotide containing at least one restriction enzyme recognition site. Preferable restriction enzymes are either EcoRI or NotI. A preferred sequence of the polynucleotide is as follows: 5'-AGCTGAATTC GCG-GCCGCAA TACGACTCAC TATAGTTTTT TTTTTTTTT TTT-3' (SEQ. ID. No.: 4). A preferred embodiment is wherein all of the above referenced bound polynucleotides are between 30 and 100 nucleotides in length.

In still another embodiment of the current invention, a ds-cDNA-immobilized support, made of ds-cDNA bound to an insoluble support, preferably an ID wherein at least one strand of the ds-cDNA contains at least one sequence complementary to the polyadenylic acid tail of mRNA. In a prefered embodiment of this invention, at least one strand of the ds-cDNA contains a RNA promoter, with a more preferable embodiment being wherein the ds-cDNA contains at least two different RNA promoters. More preferably, these promoters are either the T7 or SP6 RNA promoter. In an alternative embodiment of this ds-cDNA-immobilized support, at least one restriction enzyme recognition site is incorporated into the sequence.

Another separate embodiment of the current invention is a method for producing a ds-cDNA-immobilized support by binding a polynucleotide, preferably containing at least one RNA promoter, to an insoluble support. The polynucleotide preferably contains at least one sequence complementary to the polyadenylic acid tail of mRNA, thereby creating a nucleotide-immobilized support. Thereafter adding a solution, such as a cell lysate, containing polyadenylated mRNA to the nucleotide-immobilized support and permitting the polyadenylic acid tail of the mRNA to hybridize with the bound complementary sequence, and more preferably incubating the support and solution, thereby creating a first liquid phase and a solid phase. In a more preferable embodiment of the above method, the first liquid phase is removed after incubation. After hybridization, produce antisense cDNA complementary to the annealed mRNA, then produce sense cDNA complementary to previously produced antisense cDNA.

The highly prefered embodiment of the above method entails using reverse transcriptase, dATP, dCTP, dGTP and dTTP in the first reaction mixture, and then incubating the solid phase and first reaction mixture. After incubation, a second reaction mixture is added to the incubated solid phase containing RNase, DNA polymerase, DNA ligase, dATP, dCTP, dGTP and dTTP. Thereafter it is preferable to incubate the solid phase thereby resulting in a second liquid phase and then remove the second liquid phase.

One further embodiment of the present invention is drawn to a method for storing ds-cDNA which preserves the ds-cDNA by producing a ds-cDNA-immobilized support, removing any liquid from the support and thereafter storing the ds-cDNA-immobilized support.

Other alternative embodiments of the invention are of a method for producing antisense mRNA on a solid support, by producing a ds-cDNA-immobilized support as described above wherein the ds-cDNA bound to the support additionally contains a RNA promoter. Thereafter produce antisense mRNA by adding a sample solution containing reagents which will allow the promoter to initiate transcription. The prefered method of producing antisense mRNA is, however, by incubating the support and sample solution, thereby creating a first liquid phase and a solid phase, and wherein the following steps are used to begin the reaction:

1) Add a reaction mixture to the solid phase containing RNA polymerase, ATP, CTP, GTP and UTP with preferably one of the dNTP's being labeled.

2) Incubate the solid phase and reaction mixture then and heat the solid phase and reaction mixture, thereby creating a liquid phase containing antisense mRNA.

Therafter it is prefered to continue the reaction by obtaining the liquid phase and treating it with DNase.

Another embodiment of the present invention is drawn to a method for producing sense mRNA on a solid support by the following steps:

(a) binding a polynucleotide with at least one sequence complementary to the polyadenylic acid tail of mRNA, at least one RNA promoter, and at least one restriction enzyme recognition site to an insoluble support, thereby creating a nucleotide-immobilized support;

(b) adding a sample solution containing mRNA with a polyadenylic acid tail to the nucleotide-immobilized support;

(c) permitting the polyadenylic acid tail of the mRNA to hybridize with the complementary sequence;

(d) using the mRNA as a template to produce antisense cDNA complementary to the mRNA;

(e) producing sense cDNA complementary to the antisense cDNA, thereby creating a ds-cDNA molecule immobilized to the support;

(f) adding a double stranded adaptor to the ds-cDNA, the adaptor containing at least one of each of the following: a second RNA promoter different from that on the polynucleotide bound to the insoluble support, and a second restriction enzyme recognition site different from the restriction enzyme recognition site on the polynucleotide bound to the insoluble support. Optionally, the reaction mixture can be added to the solid phase containing DNA ligase and the double stranded adaptor;

(g) digesting the ds-cDNA with a restriction enzyme which recognizes the second restriction enzyme recognition site;

(h) producing a DNA/RNA duplex by transcribing RNA using the second RNA promoter. This reaction can be carried out by adding a mixture to the solid phase containing ATP, CTP, GTP and UTP, and an RNA polymerase which reacts with the second RNA promoter and thereafter incubating the solid phase and reaction mixture creating a DNA/RNA duplex. Optionally, one of the aforementioned dNTP's can be labeled; and (i) denaturing, preferably through heating, the DNA/RNA duplex, thereby creating a liquid phase containing sense mRNA and optionally treating the liquid phase with DNase.

Other Alternative embodiments of the present invention are drawn to methods of producing ds-cDNA by the following steps:

1. adding a sample solution containing mRNA to a nucleotide-immobilized support;

2. incubating the sample solution and support, thereby creating a first liquid phase and a solid phase;

3. removing the first liquid phase;

4. adding a first reaction mixture containing reverse transcriptase, dATP, dCTP, dGTP, and dTTP to the solid phase, with one of the aforementioned nucleotides being labeled;

5. incubating the first reaction mixture and solid phase;

6. adding a second reaction mixture containing RNase, DNA polymerase, DNA ligase, dATP, dCTP, dGTP, and dTTP to the solid phase; and 7. incubating the second reaction mixture and solid phase.

One other embodiment of the current invention is a method for producing sense ss-cDNA by creating ds-cDNA according to the method described above, then heating the second reaction mixture and solid phase. Thereby a second liquid phase will be created containing the obtainable sense ss-cDNA.

Other prefered embodiments of the current invention are to methods of producing antisense ss-cDNA by producing ds-cDNA as described above, then heating the second reaction mixture and solid phase, thereby creating a second liquid phase containing the sense ss-cDNA and thereafter obtaining the antisense ss-cDNA containing solid phase.

One other similar embodiment is a method for producing sense ss-cDNA by using the ds-cDNA-immobilized support described above. After the sense cDNA and antisense cDNA have been allowed to form a ds-cDNA duplex in the liquid phase, the ds-cDNA is denatured, and the liquid phase is obtained.

Other similar embodiments of the current invention are drawn to a method for producing sense ss-cDNA. These methods include producing a ds-cDNA-immobilized support in a liquid phase, wherein one strand of the ds-cDNA is bound to an insoluble support, and one strand of the ds-cDNA also contains at least one sequence complementary to the polyadenylic acid tail of mRNA. Thereafter, denature the ds-cDNA-immobilized support and obtain the liquid phase.

One further embodiment of the present invention is a method for producing antisense ss-cDNA, by producing a ds-cDNA-immobilized support as described above, wherein the sense cDNA and antisense cDNA form a ds-cDNA duplex in the liquid phase. Preferably, the ds-cDNA contains a restriction enzyme site, which can optionally be cleaved in this method. After denaturing the ds-cDNA and removing the liquid phase, the resulting solid phase will contain the antisense ss-cDNA.

Other embodiments of this invention describe methods of manipulating cDNA vectors by placing cDNA sequence into a vector in a particular orientation. One method is performed using the following steps:

(a) producing a ds-cDNA-immobilized support as described above, wherein a polynucleotide bound to an insoluble support additionally contains a first restriction enzyme recognition site;

(b) adding a double stranded adaptor to the ds-cDNA, the adaptor containing a second restriction enzyme recognition site different from the restriction enzyme recognition site on the polynucleotide bound to the insoluble support;

(c) digesting the ds-cDNA with a restriction enzyme which recognizes the first restriction enzyme recognition site, and with a restriction enzyme which recognizes the second restriction enzyme recognition site, thereby resulting in a non-bound ds-cDNA having a first sticky end at a first end thereof and preferably also a second sticky end at a second end thereof;

(d) ligating the non-bound ds-cDNA to a vector having sequences complementary to the first sticky end at a first end thereof and preferably also sequences complementary to the second sticky end at a second end thereof.

An additional aspect of the current invention is drawn to a method of immobilizing a first single stranded polynucleotide having at least one purine base to an insoluble support having an exposed sulfhydryl residue by hybridizing the first single stranded polynucleotide with a second single stranded polynucleotide in order to form a double stranded complex. The support is optionally treated with a primary amine compound. This complex will thereby protect the purine base from further reaction. Thereafter, react the 5' end of the first polynucleotide, preferably after denaturing the double stranded complex, with a maleimide compound to produce a polynucleotide having a maleimide group at its 5' end. One optional maleimide compounde is sulfo-SMCC. Further reactions will attach the maleimide group at the 5' end of the first polynucleotide with the sulfhydrl residue bound to the insoluble support.

In the method of attaching a polynucleotide to an insoluble support as described above, one prefered embodiment is wherein the sulfhydryl residue is produced from an exposed amine residue on the insoluble support by reacting the amine residue with SATA to form a reacted complex. Deacetylation of the reacted complex is then performed with hydroxylamine.

DETAILED DESCRIPTION

Definitions

Figure 1:
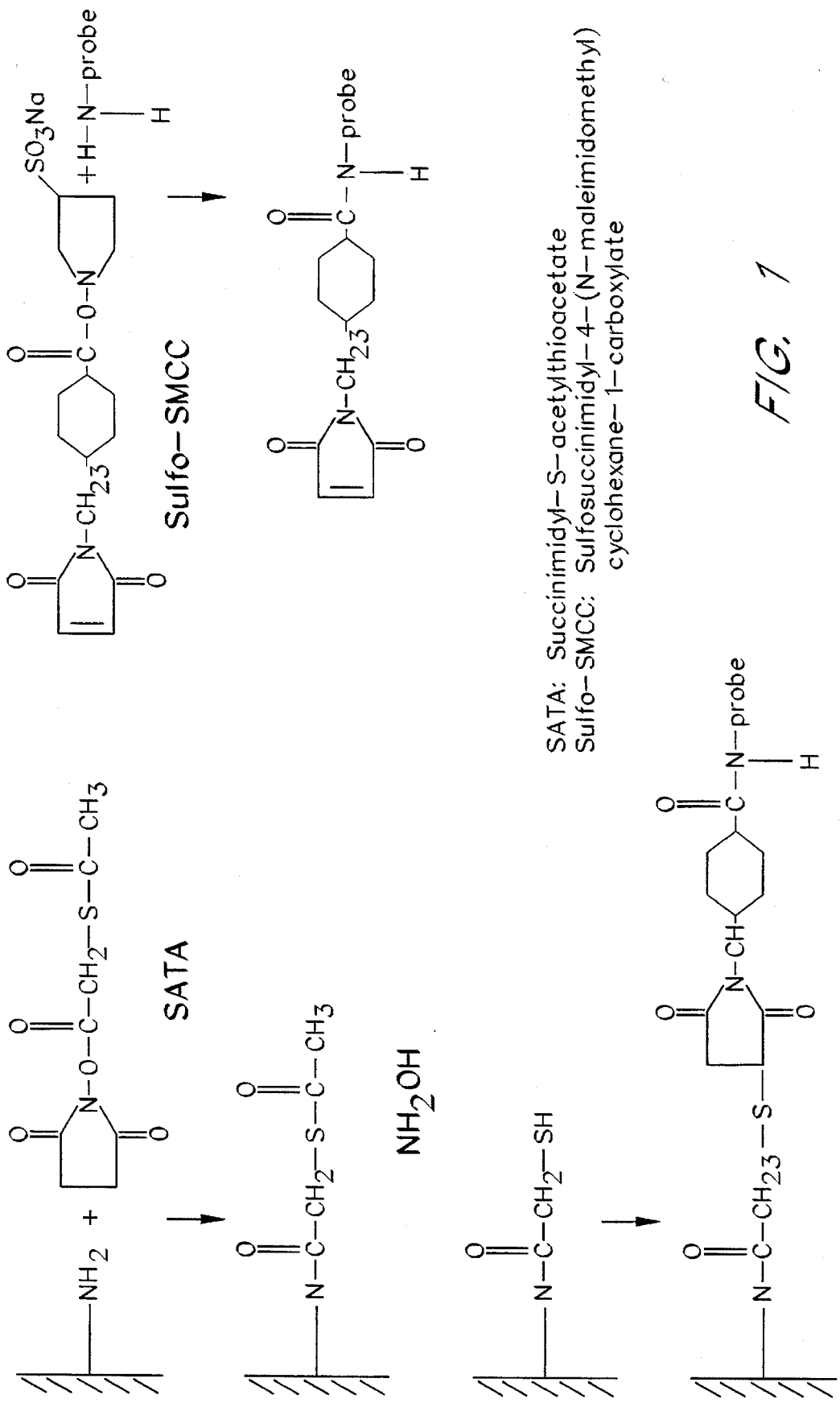
FIG. 1 illustrates an immobilization procedure of a first polynucleotide probe onto insoluble supports by the maleimide method.

The following well-known abbreviations are used herein:
A: adeninc
C: cytosine
G: guanine
T: thymine
U: uracil
dATP: deoxyadenosine triphosphate
dCTP: deoxycytidine triphosphate
dGTP: deoxyguanosine triphosphate
dTTP: deoxythymidine triphosphate.

For the purpose of this invention, an "Insoluble Dish" is defined as a concave or flat support device that is insoluble in the water-based buffers and solutions commonly used in the production of oligonucleotides. Preferably, the Insoluble Dish used in the present invention is capable of holding liquids. Thus, a preferred embodiment includes a microtiter dish, a plastic plate or a nylon membrane, but not, for example a plastic or other insoluble bead.

Nucleotide sequences which can be specifically digested by restriction endonuclease enzymes are defined herein as "restriction enzyme recognition sites." A large number of such recognition sites are known, and a given sequence may contain more than one recognition site. For example, some sequences might contain the recognition site for both NotI and for EcoRI.

An "RNA promoter" is defined herein as a nucleotide sequence which is recognized by RNA polymerase and can initiate transcription of nucleotides downstream therefrom. For example, the nucleotide sequence of the T7 promoter (Seq ID No. 1) is shown below:

5'-AATACGACTCACTATAG-3'.

Another example of an RNA promoter is the SP 6 promoter (Seq ID No. 2), shown below:

5'-CATTTAGGTGACACTATAGAA-3'.

An "insoluble support" is defined herein as a material which does not substantially dissolve in the solution used during a given procedure, and is not melted or dissolved during a heating procedure used in procedures within the scope of the present invention. Examples of insoluble supports would include an Insoluble Dish (including such supports as plastic microtiter plates, glass microtiter plates and nylon membranes), and would also include agarose and plastic beads.

In this invention, sense mRNA refers to the mRNA identical to the genetic information, while the antisense mRNA refers to a polynucleotide complementary to the sense mRNA. The sense ss-cDNA contains the identical genetic information to that of sense mRNA, although, in the cDNA the uracil bases in the mRNA are changed to thymine, and the nucleotides are deoxyribonucleotides, not ribonucleotides.

The water which is used in this invention is preferably treated with diethylpyrocarbonate (DEPC) in order to substantially reduce the activity of RNase therein. The DEPC treatment of water can be performed by adding 0.1% DEPC to water, incubating at 37° C. overnight, followed by autoclaving.

Overview of the Present Invention

Using the present invention, ds-cDNA, ss-cDNA, sense mRNA, and antisense mRNA can be quickly and advantageously synthesized in an Insoluble Dish (ID) such as a microtiter plate from bound oligonucleotide sequences. The advantage of this system lies in the ease of changing solutions when the RNA is bound to an ID. Previously, ethanol precipitations or similar proceedures have been required with every solution change to recover the soluble RNA. In the preferred embodiment of the present invention, nucleotide sequences containing restriction enzyme sites, RNA promoter sequences and poly (dT) sequences are covalently bound to wells of a microtiter plate. Cell lysates containing cytoplasmic mRNA can be placed into the wells without further purification. In the preferred embodiment, an oligo (dT) nucleotide strand will hydrogen bond with the poly(A) tail of mRNA. While the mRNA is immobilized by being annealed to its target, solution changes which do not interfere with the hybridization conditions can be performed.

Single-stranded-cDNA can be made from immobilized mRNA by adding deoxynucleotides and reverse transcriptase. Double-stranded-cDNA can then easily be produced by changing the medium to one containing DNA polymerase and deoxyoligonucleotides. Antisense mRNA can be transcribed by adding RNA polymerase targeted to the promoter binding site on the covalently linked oligonucleotide. Furthermore, adapters containing different restriction enzyme recognition sites and a second RNA promoter sequence can be preferably and advantageously ligated to the free end of the ds-cDNA.

Thereafter, sense mRNA can be transcribed quickly and easily by adding a RNA polymerase targeted to the ligated adapter. Single stranded sense cDNA can be repeatedly synthesized from immobilized single stranded antisense cDNA. This invention provides a useful tool for not only basic molecular biology and analysis. This invention can also be used for the molecular diagnosis and treatment in various diseases.

We have discovered that immobilization of polynucleotide sequences to an insoluble support containing at least one sequence complementary to a polyadenylic acid tail of mRNA can provide significant advantages in a variety of nucleotide synthesis and processing techniques useful in both theoretical and applied molecular biology. Many of these advantages will be made apparent from the ensuing description of the invention.

Bound Polynucleotides of the Present Invention

As discussed above, the immobilized oligonucleotides include nucleotide sequences complementary to the mRNA polyadenylic acid tail. Such complementary sequences would include oligo (dT) as well as poly-U. It is preferable that the length of such sequences be between 15 and 80 bases, and more preferably between 30 and 100 bases.

Polynucleotide sequences of various lengths, including 30 to 100-mers, can be readily synthesized using techniques known to those of ordinary skill in the art. These techniques include methods for the synthesis of sequences having sequences complementary to the polyadenylic acid tail of mRNA, having an RNA promoter sequence, and/or having various restriction enzyme recognition sites. A DNA synthesizer can be used to expedite such synthesis. One such DNA synthesizer is manufactured by Applied Biosystems of Los Angeles, Calif.

In a preferred embodiment of the present invention, the polynucleotides including at least one sequence complementary to a polyadenylic acid tail of mRNA are bound to an insoluble support to create a nucleotide-immobilized support. Preferably, these sequences are from 30 to 100 nucleotides in length. In an especially preferred embodiment, the immoblized polynucleotides also include an RNA promoter, and/or restriction enzyme recognition sites. Preferably, the 5'-terminal end is bound to the insoluble support while the 3'-terminal end hybridizes to the polyadenylic acid tail of mRNA.

Thus, we have used a number of different polynucleotide sequences for immobilization. One particular sequence preferred sequence includes a poly (dT) sequence, Eco RI and Not I recognition sequences and the T7 promoter. The use of this sequence is described in many of the examples provided herein. However, we have also used other combinations of restriction enzyme recognition sites and promoters with similar results. For example, the use of Sma I-Sal I with the T7 promoter does not appear to significantly effect any of the methods described herein. We have also used Eco RI-Not I with the SP6 promoter.

Immobilization Methods

In the practice of the present invention, polynucleotides are immobilized onto an insoluble support. Various methods of immobilizing polynucleotides to the insoluble support are available, including covalent binding, ionic binding, and the physical absorbance method. However, the covalent binding method is preferred. Thus, in certain embodiments of the present invention, the polynucleotides are immobilized to microtiter plates which exhibit functional groups, such as carboxyl residues, amine residues, or hydroxyl residues on the surface thereof. Plastic plates exhibiting carboxyl residues or primary amine residues on the surface, or plastic plates which do not have these functional groups on the surface, but have them added later can also be used. Preferably, plastic plates which already express carboxyl residues or primary amine residues on the surface are used. Examples of plastic plates containing carboxyl residues and primary amine residues on the surface are the "Sumilon" microplates MS-3796F and MS-3696F, available from Sumitomo Bakelite.

In a preferred procedure for immobilization of the polynucleotide to an insoluble support exhibiting a functional group, the 5'-terminal end of the polynucleotide is covalently linked to the functional group. Any of a variety of methods for covalent binding of polynucleotides to these functional groups can be used. Examples of preferred well-known methods include the maleimide method and carbodiimide method.

The maleimide method, illustrated in FIG. 1, involves the reaction between a substance containing a maleimide group and another material containing a sulfhydryl residue (SH). In order to attach the 5' end of a polynucleotide to an immobilized support using the maleimide method, the 5' end of the polynucleotide is reacted with a maleimide compound. A suitable maleimide compound is sulfosuccinimidyl-4-(N-maleimidomethyl)cyclohexane-1-carboxylate (sulfo-SMCC).

The SH residue is provided on the support by a reaction between a support having an amine residue and succinimidyl-S-acetylthioacetate (SATA), followed by deacetylation using hydroxylamine ($NH_2OH$). (Sulfo-SMCC and SATA are readily available from a variety of commercial sources, including the Pierce Company.) The resulting SH group on the support can then react with the maleimide group on the 5' end of the polynucleotide to form a polynucleotide-immobilized support. One problem we have experienced in the use of the maleimide method is that the SH group on the plate can react not only with an amine group at the 5' end of the polynucleotide, but can also react with primary amine groups on the purine bases, adenine and guanine. In order to assure that the polynucleotides are mobilized at their 5' ends, the amine groups on the purine bases can be protected by pairing the polynucleotide to a complementary polynucleotide prior to immobilization. After immobilization, the complementary polynucleotide can be removed through denaturation, such as through heating.

Figure 2:
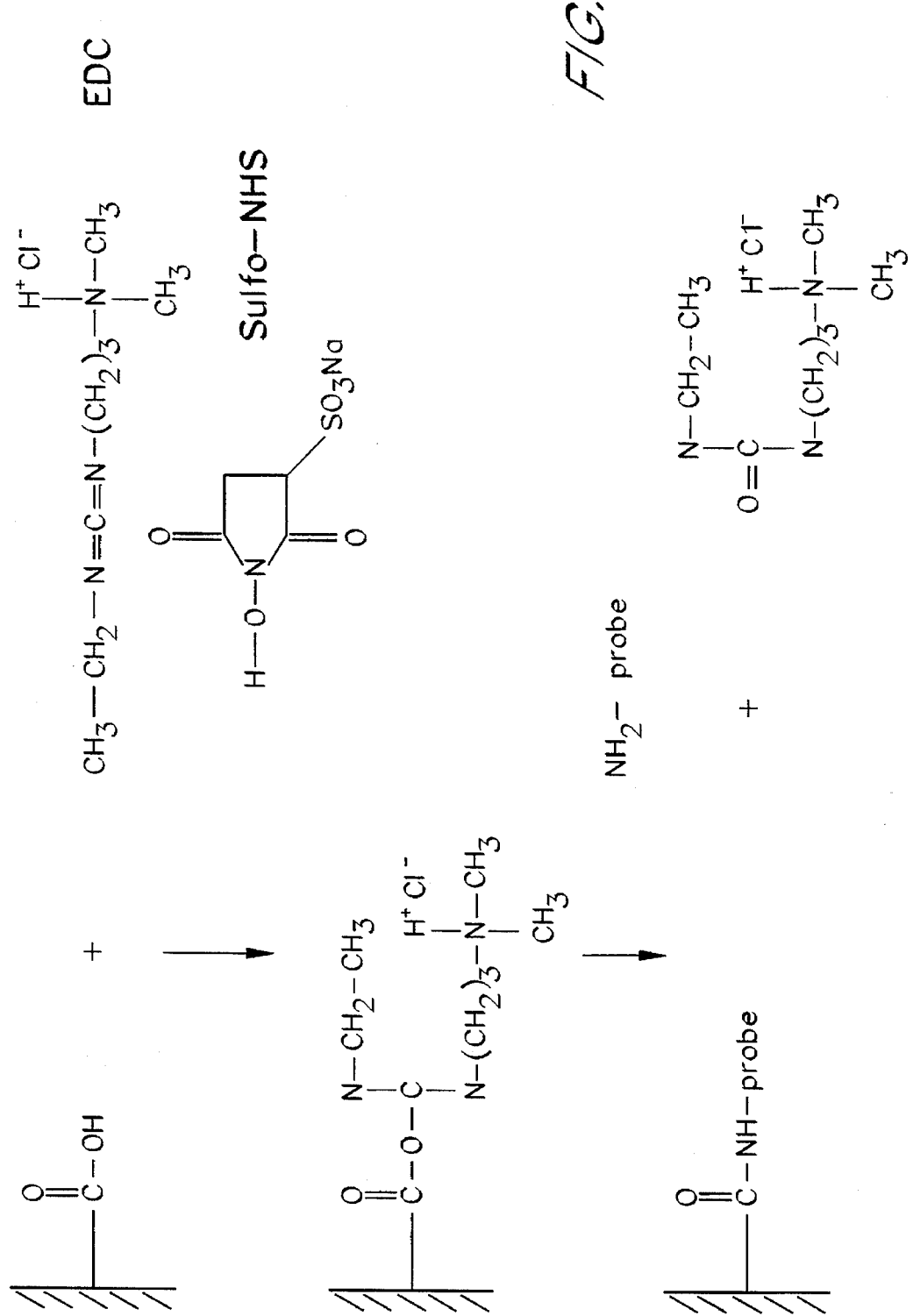
FIG. 2 illustrates an immobilization procedure of a first nucleotide probe onto insoluble supports by the carbodiimide method.
Figure 3A:
FIG. 3 shows the overall principle of the procedure of synthesis of sense ss-cDNA, antisense mRNA and sense mRNA from the polynucleotide-immobilized support in this invention.
Figure 3B:
Figure 3C:
Figure 3D:
Figures 3E, 3F:
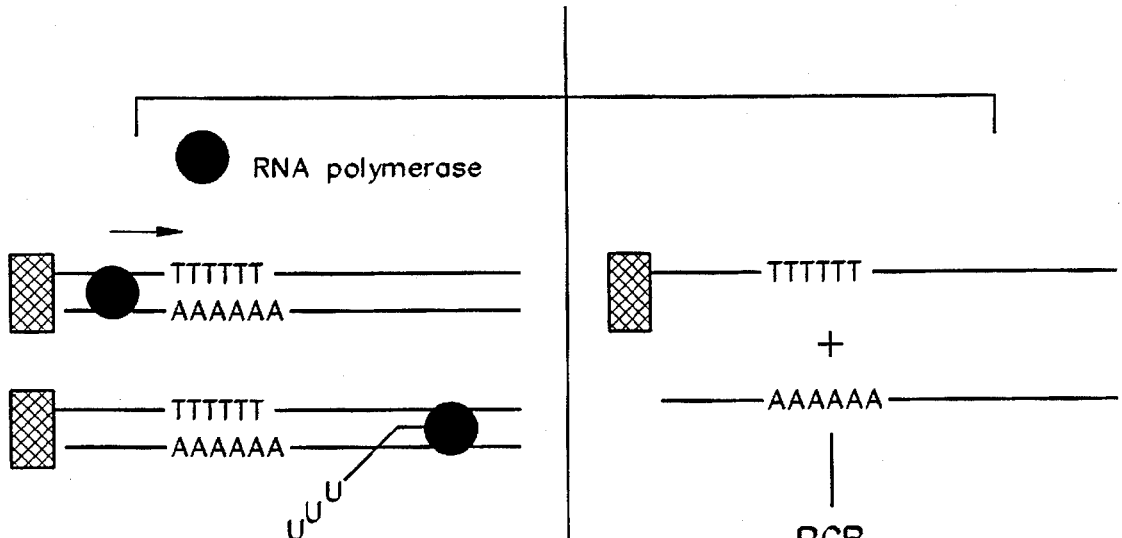
Figure 3G:
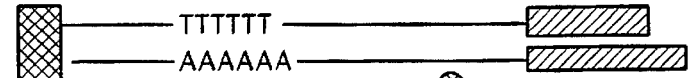
Figure 3H:
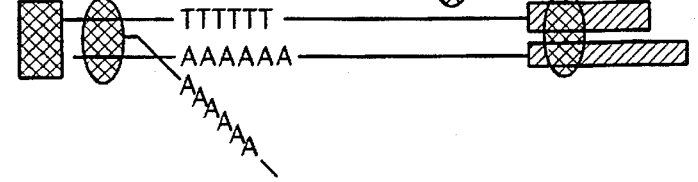

The carbodiimide method is illustrated in FIG. 2. This method involves a reaction between a carbodiimide compound with an amine residue and a material containing a carboxyl residue. An example of a carbodiimide compound is 1-ethyl-3-(3-dimethyl-aminopropyl)carbodiimide hydrochloride (hereafter called EDC). In order to use EDC in the carbodiimide method, it must first be activated to an EDC compound containing an amine residue. This can be done by reaction with N-hydroxysulfosuccinimide (hereafter called Sulfo-NHS). Both EDC and Sulfo-NHS are available from well known commercial sources, including the Pierce Company.

In the practice of a preferred carbodiimide method for attaching polynucleotides to a support, a support having a carboxyl residue attached is used. EDC is activated by reaction with Sulfo-NHS. This activated EDC is reacted with support containing surface bound carboxyl residues. This can then be reacted with polynucleotides having an amine residue at their 5'-terminal ends, resulting in a polynucleotide-immobilized support.

We have found that non-specific binding of activated amine or carboxyl residues on insoluble supports can be effectively reduced or eliminated by treating plates to which polynucleotides have been immobilized with a primary amine compound, preferably glycine.

A large number of other immobilization methods can be used, including the biotin-avidin system described by Terada, et al., supra.

Application of Sample

In the preferred methods of the present invention, a sample containing mRNA is applied to the insoluble support to which a polynucleotide having a sequence complementary to a polyadenylic acid tail of mRNA has been bound. The polyadenylic acid tail of mRNA in the sample is allowed to hybridize with the bound polynucleotide. This can be accomplished by incubation at temperature dependent on a variety of factors, as is well known to those with ordinary skill in the art. These factors include the length of complementary nucleotide sequences, the ratio of Guanine or Cytosine (GC contents) within the entire base content in the complementary nucleotide sequences (which will be 0% if only the polyadenylic acid tail is complementary), the NaCl concentration in buffer, the number of bases which mismatch in the complementary nucleotide sequence, and the type of nucleotide. In a preferred form of this invention, the following equation can be used to calculate the preferred incubation temperature:

$$T_{inc}=16.6\times\log (M)+0.41(GC)+81.5-67.5/n-15(°C.).$$

In the equation shown above, M is the NaCl concentration (M) in solution, GC represents GC contents (%), n represents the length of nucleotide sequences (the number of nucleotides).

The incubation time can also be determined according to methods described in the Molecular Cloning manual.

The time for incubation is preferably from 1 hour to overnight, and the sample should preferably be gently swung during incubation. Incubation is preferably performed in an appropriate buffer solution. The same buffer used to hybridize RNA and DNA in the Northern Blot or the Dot Blot Methods can be used. The buffer is preferably prepared in a way so as not to contaminate it with RNase. If any RNase contamination is present, the activation thereof should be controlled to be as low as possible. RNase-free buffers are commercially available, such as those available within mRNA purification kits, such as those sold under the trademark "FastTrack" by InVitrogen of San Diego, Calif., or lysis buffer, which is described hereinbelow.

As stated above, in order to eliminate RNase activity from water used in the methods of this invention, the water is preferably treated with Diethylpyrocarbonate (DEPC). The preferred DEPC treatment involves addition of 0.1% DEPC to the water, followed by storage overnight at 37° C. and sterilization in an autoclave.

Washing Procedures

Preferably, after incubation, unbound components of the sample are washed from the insoluble support. Appropriate solutions for washing include the incubation buffer or the buffer included in the mRNA purification kit. However, it is preferable to use a proper solution depending on the type of nucleic acid. In order to retain mRNA, the washing solution is preferably DEPC-treated 20 mM Tris, pH 7.5 containing 1 mM EDTA and 0.5M of NaCl (hereafter called RNA washing solution). To retain DNA, the washing solution can be autoclaved 20 mM Tris, pH 7.5 containing 1 mM EDTA and 0.5M of NaCl (hereafter called DNA washing solution).

Double-Stranded-cDNA Immobilized Support

The ds-cDNA immobilized support in this invention can be obtained as shown below. The polynucleotide-immobilized support is mixed with a mRNA sample allowing hybridization between the bound polynucleotide and the mRNA to occur. cDNA is then synthesized from the mRNA template using reverse transcriptase. The mRNA is preferably digested with RNase H, and ds-cDNA is then synthesized, preferably by DNA polymerase, the four dXTP's and ligase. As a result, a construct of ds-cDNA immobilized to the insoluble support is formed.

The complementary strand of DNA produced can be labeled by incorporating labeled dXTP's during the production thereof. Any of a variety of labels can be used, for example, radionuclides or agents, such as biotin, which can be detected by subsequent colorimetric or light-emitting reactions.

The bound cDNA can be used for a variety of further techniques. In accordance with a particular preferred method of the present invention, antisense RNA can be produced if the bound polynucleotide contains an RNA promoter sequence. An appropriate RNA polymerase for the promoter is added along with the four ribonucleotide triphosphates. As will be apparent to those with ordinary skill in the art, this antisense RNA can be labeled if at least one of these nucleotide triphosphates bears a label.

In accordance with an additional preferred method of the present invention, an analysis equivalent to RNA blot analysis can be performed by allowing a sample to hybridize with the bound antisense ss-cDNA resulting after heat denaturation. After heat denaturation, the sense ss-cDNA will be in the liquid phase. This sense ss-cDNA can be used for a variety of well-known techniques, such as PCR and sequencing.

The mRNA used in these experiments are preferably purified RNA, mRNA from biological samples, or RNase inhibited cell lysates. The purification of mRNA follows the current mRNA purification protocol used for Northern blot or dot blot methods. Commercial kits are also available. For procedures involving RNase inhibited cell lysates, a lysis buffer is preferably used in which the biological material is treated with a pH 8.0 solution containing 200 µg/ml of Proteinase K and 10 mM of Vanadyl ribonucleoside complex, 500 units/ml of RNase inhibitor, 0.5% of sodium dodecyl sulfate (SDS), and ethylene diamine tetra acetate (EDTA).

The incubation temperature vaires in each case depending on whether the experiment is a hybridization of nucleic acids or enzymatic reaction. Hybridization is performed as described above in the section entitled Application of Sample.

In the case of an enzymatic reaction, any temperature in which the enzyme is not mostly inhibited is acceptable, however, preferably the optimum temperature for each enzyme is used. The incubation time can be from 30 minutes to overnight either with or without shaking. In enzymatic reactions, any buffer which will not mostly inhibit enzyme activity is acceptable, however, the optimum buffer components for each enzyme activity are most preferable. It is important however not to contaminate any of the buffers with RNase. If RNase is present, its activities should be controlled with inhibitors such as RNAsin to be as minimal as possible.

In addition, heating reactions, such as for denaturation of double-stranded polynucleotide complexes, are done in appropriate buffer solutions.

The insoluble support containing immobilized ds-cDNA can be stored for at least one month at 4° C. under conditions where the solution is not contaminated with DNase and consists of preferably 20 mM Tris-hydrochloride, pH 7.6 containing 1 mM EDTA and 0.5M NaCl.

The insoluble supports having immobilized polynucleotide can be reused many times. In fact, we have reused the nucleotide-immobilized supports many times without significant loss of bound nucleotide. Digestion and removal of hybridized mRNA from the cDNA for reuse of the bound polynucleotide can be conducted by rinsing with a RNase containing solution after incubation. A mild NaOH solution in place of the RNase containing solution can also be used to remove hybridized mRNA from bound cDNA.

Second RNA Promoter and Sense RNA Synthesis

In certain embodiments of the methods of the present this invention, a second RNA is promoter is desired. This second RNA promoter can be used to direct the production of sense RNA. Use of labeled nucleotide triphosphates can be used to produce labeled sense RNA. The nucleotide sequence of the second RNA promoter is a sequence recognized by RNA polymerase that can be used to initiate transcription of the subsequent downstream genetic information. The second RNA promoter is generally located on the opposite side of the ds-cDNA from the first promoter. These sequences preferably encode the binding site of a different promoter than the first promoter sequence in the polynucleotide-immobilized insoluble support. In this invention, the RNA polymerase which reacts with second RNA promoter should not cross react with the first RNA promoter sequence. If the first RNA promoter is for example, from the bacteriophage T7, the second promoter can be, for example, the SP6 promoter.

In order to provide a second promoter, an adaptor can be used which contains both the second RNA promoter and a second restriction enzyme recognition site. This adaptor can then be added to the end of the ds-cDNA. An example of an appropriate adaptor is the SalI-SP6 adaptor, as shown below (Seq ID No. 3):

```
5'-TCGACATTTAGGTGACACTATAGAA-3'
3'-     GTAAATCCACTGTGATATCTT-5'
```

The second restriction enzyme recognition site should preferably not be the same sequences as those in the polynucleotide-immobilized insoluble support or the directionality of the digested mRNA will be lost. If the first restriction enzymes are, for example EcoRI and/or NotI, the second restriction enzymes could be SmaI and/or SalI.

Directional Cloning

A ds-cDNA molecule containing a first restriction enzyme site at one end and second restriction enzyme site at the other can be prepared by blunt end ligation. In this method, double stranded oligonucleotides containing a restriction enzyme site and RNA promoter sequence are ligated to the unbound end of the ds-cDNA using an enzyme such as T4 ligase. The resultant modified ds-cDNA can be inserted into a linearized vector containing both restriction enzyme sites. Because the first and second restriction enzyme sites are disimilar, the ds-cDNA ligation will be unidirectional. In this way the direction of cDNA insertion into the vector can be controlled.

Schematic Examplary Uses of the Invention

A schematic representation of a preferred embodiment of the present invention is shown in FIG. 3. The insoluble immobilized support (a) containing a 30–100-mer polynucleotide sequence having a restriction enzyme recognition site, an RNA promoter and a oligo (dT) sequence is mixed with the sample solution containing polyadenelated mRNA. The resultant immobilized polynucleotide-mRNA complex is reacted with reverse transcriptase using the oligo (dT) tail of the bound nucleotides as a primer and the mRNA as a template. As a result, a mRNA-cDNA hybrid is synthesized on the insoluble support (c). RNase and DNA polymerase addition causes digestion of the RNA and conversion of the mRNA-cDNA hybrid into ds-cDNA affixed to the insoluble support (d). This immobilized ds-cDNA is then incubated at a low salt concentration in, for example, water, and then heated to denature the ds-cDNA. The sense ss-cDNA will be unable to maintain hydrogen bonding with its homologous pair and float free in solution (e). The unbound sense ss-cDNA (e) can thereafter be used as a PCR template to amplify specific genes of interest.

An alternative use of the aforementioned ds-cDNA immobilized support (d) is to produce antisense mRNA (f). RNA polymerase specific for the antisense strand of the ds-cDNA is used to transcribe RNA molecules. Antisense mRNA is then isolated by heating the microtiter plate, removing the liquid phase, and digesting with RNase-free DNase (f).

A further embodiment of the present invention uses the ds-cDNA immobilized support (d) as a ligation target for double stranded oligonucleotides. These oligonucleotides preferably contain nucleotide sequences corresponding to a second RNA promoter and second restriction enzyme site (g). This complex (g) can then be used to synthesize sense mRNA by incubating with the RNA polymerase which transcribes from the second promoter. Sense mRNA is then isolated by heating the microtiter plate, removing the liquid phase, and digesting the liquid phase with RNase-free DNase (h).

Various aspects of the invention are explained in more detail with reference to the following examples. These examples are intended solely to illustrate the invention, and not to limit the invention in any manner.

EXAMPLE 1

Synthesis of ss-cDNA, ds-cDNA, sense and antisense mRNA, and PCR amplification of Gs protein-specific ds-cDNA from in vitro synthesized Gs protein-specific mRNA.

(1) Synthesis of polydeoxyribonucleotide. A 53-mer polydeoxyribonucleotide containing two different restriction enzyme sites, EcoRI and NotI, the T7 RNA promoter sequence, and a series of 17 thymine residues from the 5' to 3' end were synthesized using a DNA synthesizer (Model 380B, Applied Biosystems). The sequence of this polydeoxyribonucleotide (Seq ID No. 4) is as follows:

```
5'-AGCTGAATTC GCGGCCGCAA TACGACTCAC TAT-
   AGTTTTT TTTTTTTTTT TTT-3'
```

According to the Applied Biosystems' protocol, a primary amine residue was also introduced at 5' end of this polydeoxyribonucleotide by using "Aminolink-2", (Applied Biosystems). After synthesis, the polydeoxyribonucleotide was treated with approximately 30% ammonium hydroxide at 55° C. overnight, dried by a Speed-vac vacuum centrifuge (Savant), resuspended in DEPC-treated water at 1 mg/ml, then stored at −20° C.

(2) Immobilization of polydeoxyribonucleotide onto the microtiter plate. 24 μl each of 20 mM EDC (Pierce) and 10 mM sulfo-NHS (Pierce) prepared in DEPC-water were mixed with 2 μl (2 μg) of the synthesized polydeoxyribonucleotide from step (1), and added into a microtiter plate well (MS-3796F, Sumitomo-bakelite). After incubation at 37° C. overnight, the reaction solution was replaced with 20 mM Tris, pH 7.6 containing 1 mM EDTA and 0.5M NaCl and stored at 4° C.

(3) Preparation of mRNA. Rat mRNA for the Gs protein was prepared as follows:

100 μg of the plasmid vector pGEM2 containing rat Gs protein cDNA was provided by Dr. R. R. Reed (John Hopkins University). The plasmid was linearized with 1000 units of Nhe (Promega) at 37° C. for 2 hours. After extraction with an equal volume of a mixture containing Tris, pH 7.4-saturated phenol, chloroform, isoamylalcohol at a ratio of 25:24:1, the DNA was precipitated on dry ice for 30 min by addition of 0.1 volumes of 3M sodium acetate and 2.5 volumes of ice-cold ethanol. The DNA was centrifuged at 15,000 rpm for 20 min at 4° C. (MTX-150, Tomy).

The pellet was resuspended in 1 ml of 70% ethanol and recentrifuged at 15,000 rpm for 5 min at 4° C. After removal of the supernatant, the pellet was dried in a Speed-vac vacuum centrifuge (Savant) and resuspended in DEPC-water. Into the same tube, 20 µl of 5× RNA transcription buffer (Promega), 10 µl of 100 mM DTT, 100 units of RNase inhibitor (RNasin, Promega), 20 µl of 2.5 mM ribonucleotide mixture (Promega), and 100 units of T7 RNA polymerase (Promega) was added. The final volume was adjusted to 100 µl by addition of DEPC water. After incubatation at 37° C. for 2 hours, 100 units (100 µl) of RNase-free DNase (Promega) was added and the reaction was continued at 37° C. for an additional 30 minutes.

After DNA digestion, the reaction mixture was then extracted once with an equal volume of a mixture containing water-saturated phenol, chloroform, and isoamylalcohol at a ratio of 25:24:1. The synthesized RNA was precipitated on dry ice for 30 min by adding 0.1 volume of 3M sodium acetate and 2.5 volume of ice-cold ethanol. The RNA was then centrifuged at 15,000 rpm for 20 min at 4° C. (MTX-150, Tomy), and the pellet was resuspended in 1 ml of 70% ethanol and recentrifuged at 15,000 rpm for 5 min at 4° C. After removal of the supernatant, the pellet was dried in a Speed-vac vacuum centrifuge (Savant), and resuspended in DEPC-water. The optical density of this RNA was determined by spectrophotometry at a wavelength of 260 nm (U-2000, Hitachi).

The RNA concentration was adjusted at 1 mg/ml based upon the calculation of 1.0 $OD_{260}$=40 µg/ml. Five µl aliquots were then stored at −70° C. until use.

(4) ds-cDNA synthesis on microtiter plates. The synthesized Gs mRNA was diluted with DEPC-water, and 5 µl samples containing 5 µg, 1 µg, 100 ng, 10 ng, 1 ng, 100 pg, 10 pg, 1 pg or 0.1 pg of Gs mRNA was mixed with 45 µl of lysis buffer and incubated at 45° C. for 1 hour to inactivate any remaining RNase activity. 5M NaCl was added into each tube to make a final NaCl concentration of 0.5M. Solutions were then placed into the polydeoxyribonucleotide-immobilized microtiter wells. After incubation at room temperature for 30 minutes to allow hybridization of the bound ologo(dT) polydeoxyribonucleotide to the poly(A) tail of the mRNA, each well was washed twice with RNA washing buffer.

After washing, 50 µl of 50 mM Tris-HCl, pH 8.3 containing 75 mM KCl, 3 mM $MgCl_2$, 10 mM DTT, 0.5 mM each of dATP, dCTP, dGTP and dTTP (in RT buffer) and 500 units of reverse transcriptase (Superscript, Gibco-BRL) was then added into each well to begin synthesis of the first cDNA strand. This reaction was incubated at 37° C. for 1 hour.

After this "first strand" cDNA synthesis, the buffer was replaced with 50 µl of 25 mM Tris-HCl, pH 7.5 containing 100 mM KCl, 5 mM $MgCl_2$, 10 mM ammonium sulfate, 0.15 mM β-nicotinic amidoadeninedinucleotide+(β-NAD+), 0.25 mM each of dATP, dCTP, dGTP and dTTP, 1.2 mM DTT, 65 units/ml DNA ligase and 250 units/ml DNA polymerase, 13 units/ml RNase H (Gibco-BRL) (dc-cDNA synthesis buffer), and incubated at 16° C. for 3 hours to synthesize ds-cDNA from the first strand synthesis previously performed. After incubation, the solution was replaced with 20 mM Tris-HCl, pH 7.6 containing 1 mM EDTA and 0.5M NaCl, and stored at 4° C.

(5) Preparation of ss-cDNA from bound nucleotides. The bound ds-cDNA synthesized as described in Paragraph (4) was washed with cDNA washing buffer 5 times, then incubated in 50 µl of DEPC-water at 80° C. for 10 minutes to heat denature the complementary cDNA strands. Solutions containing the unbound ss-DNA were immediately transferred to fresh 0.65-ml tubes, and stored at −20° C. Plates were reused for synthesizing ds-cDNA by again incubating with ds-cDNA synthesis buffer, as described in Paragraph (4) at 16° C. for 3 hours. This procedure, repeated three times, prepared three ss-cDNAs from a single well.

(6) Antisense mRNA synthesis. The ds-cDNA synthesized as described in Paragraph (4) was washed with RNA washing buffer 5 times, and incubated in 10 µl of 5× RNA transcription buffer (Promega), 5 µl of 100 mM DTT, 50 units (1.25 µl) of RNase inhibitor (RNasin, Promega), 10 µl of 10 mM ribonucleotide mixture (Promega), and 20 units (1 µl) of T7 RNA polymerase (Promega) to a final volume of 50 µl by addition of DEPC water.

After incubation at 37° C. for 1 hour to allow transcription to begin, plates were heated to 90° C. for 8 minutes, and the solutions containing unbound antisense mRNA were immediately transferred to fresh tubes. 10 units (10 µl) of RNase-free DNase (Promega) was added into the fresh tubes and the reaction continued at 37° C. for 30 minutes to digest any remaining DNA.

The reaction mixture was then extracted once with an equal volume of a mixture containing water-saturated phenol, chloroform, and isoamylalcohol at a ratio of 25:24:1. Synthesized RNA was ethanol precipitated and centrifuged at 15,000 rpm for 20 minutes at 4° C. (MTX-150, Tomy). The pellet was resuspended in 1 ml of 70% ethanol, and recentrifuged at 15,000 rpm for 5 minutes at 4° C. After removal of the supernatant the pellet was dried in a Speed-vac vacuum centrifuge (Savant), and resuspended in 5 µl DEPC-water. The resultant antisense mRNA molecules were analyzed by agarose gel electrophoresis as follows:

Five µl of mRNA was mixed with 2 µl of 0.1M MOPS pH 7.0 containing 40 mM sodium acetate, 5 mM EDTA, pH 8.0 (5× formaldehyde gel buffer), 10 µl formamide, 3.5 µl formaldehyde, and heated to 45° C. for 15 minutes The mRNA solutions were then mixed with 2 µl of 50% glycerol containing 10 mM EDTA, pH 8.0, 0.25% bromophenol blue, 0.25% xylene cyanol FF (formaldehyde gel loading buffer), 1 µl of 1 mg/ml ethidium bromide, and loaded onto a 1% agarose gel. Electrophoresis was carried out in 10 mM phosphate buffer, pH 7.0 at 100 V/6.5 cm width for approximately 1 hour. After electrophoresis, gels were exposed to UV light and flourescent RNA bands were recorded on Polaroid film.

Electrophoretic results indicated single bands in lanes of the gel that had been loaded with either the control Gs protein mRNA as described in paragraph (3), or the synthesized mRNA from this paragraph (6).

(7) Sense mRNA synthesis. Microtiter wells with bound ds-cDNA as described in paragraph (4) were washed with cDNA washing buffer 3 times, incubated in 10 µl of 5× ligase buffer (Gibco-BRL), 31 µl DEPC-water, 4 µl (4 µg) SalI-SP6 oligonucleotide adaptor (Seq ID No. 3) and 5 units (5 µl) of T4 ligase (Gibco-BRL) at 16° C. overnight.

After washin each well three times with cDNA washing buffer, 5 µl of H buffer (Boerhinger-Mannheim), 44 µl of DEPC-water and 10 units (1 µl) of SalI (Boerhinger-Mannheim) were added. This solution was incubated at 37° C. for 2 hours to allow cleavage at the SalI site. Each well was then washed with RNA washing buffer 5 times, and incubated in 10 µl of 5× RNA transcription buffer (Promega), 5 µl of 100 mM DTT, 50 units (1.25 µl) of RNase inhibitor (RNasin, Promega), 10 µl of 10 mM ribonucleotide mixture (Promega), and 20 units (1 µl) of SP6 RNA polymerase (Promega). The final volume was adjusted to 50 µl by addition of DEPC-water.

After incubating at 37° C. for 1 hour, plates were heated to 90° C. for 8 minutes, and the liquid solutions were immediately transferred to fresh tubes. 10 units (10 μl) of RNase-free DNase (Promega) was added and the reaction was continued at 37° C. for an additional 30 minutes to digest any remaining DNA. The reaction mixture was then extracted once with an equal volume of a mixture containing water-saturated phenol, chloroform, and isoamylalcohol at a ratio of 25:24:1. Synthesized RNA was ethanol precipitated and the RNA was centrifuged at 15,000 rpm for 20 minutes at 4° C. (MTX-150, Tomy). The pellet was resuspended in 1 ml of 70% ethanol and recentrifuged at 15,000 rpm for 5 minutes at 4° C. After removing the supernatant the pellet was dried and resuspended in 5 μl DEPC-water.

The resultant mRNA molecules were analyzed by agarose gel electrophoresis as described in paragraph (6), and flourescent RNA bands were recorded onto Polaroid films. Samples loaded on the gel included the control Gs protein mRNA as described in paragraph (3), and synthesized mRNA from paragraph (6) and this paragraph (7). The size of the synthesized mRNA was approximately 2000 bases, slightly larger than the control mRNA, probably due to addition of polydeoxyribonucleotides at the 3' and 5' ends of the molecule.

(8) Synthesis of PCR primers for amplification of G protein specific ds-cDNA. Sense (G2-a) and antisense (G4-as) oligodeoxyribonucleotides specific for the G protein α subunit were synthesized in a DNA synthesizer as described in paragraph (1). The nucleotide sequences are as follows:

G2-s 5'-AGCACCATTGTGAAGCAGATGA-3' (Seq ID No. 5)
G4-as 5'-CTCTGGCCTCCCACATCAAACA-3' (Seq ID No. 6)

(9) PCR amplification of cDNA. To 1 μl of ss-cDNA as described in paragraph (5), add 0.1 μg (1 μl) each of oligonucleotide primers G2-s and G4-as, 5 μl of 10× PCR buffer (Promega), 1 μl of 25 mM $MgCl_2$, 4 μl of 10 mM dNTP mixture (Promega), 0.5 μl Taq polymerase (Promega), and 36.5 μl of DEPC-water. Two drops of mineral oil were overlayered onto the reaction mixture to prevent evaporation. The reaction was first heated to 95° C. for 10 minutes, then PCR cycling was carried out in a Thermal cycler (Model 480, Perkin-Elmer Cetus) with 30 cyles of annealing at 55° C. for 1.5 minutes, extension at 72° C. for 4 minutes and denaturing at 95° C. for 1.5 minutes In a parallel experiment, Gs protein cDNA (10 ng in 1 μl) was used as a positive control. Ten μl of the resultant PCR products were mixed with 1 μl of 10× loading buffer (0.25% bromophenol blue, 0.25% xylene cyanol FF, 15% Ficoll type 400), heated to 65° C. for 5 minutes, then applied to a 1.5% agarose gel containing 5 μg/ml ethidium bromide. Electrophoresis was carried out in a 1× TBE buffer (0.045M Tris-borate buffer, pH 8.0 containing 0.001M EDTA) at 100 V/6.5 cm width for approximately 1 hour. After electrophoresis, nucleotide bands were fluoresced and recorded onto Polaroid film. Samples loaded on the gel included 5 μg, 1 μg, 100 ng, 10 ng, 1 ng, 100 pg, 10 pg, 1 pg, and 0.1 pg of starting mRNA as described in paragraph (5). A negative control lane did not contain any mRNA. Results indicated that Gs protein DNA was reproducibly amplified from starting mRNA concentrations of 10–100 pg with a size of approximately 500 base pair, similar to that of the positive control.

EXAMPLE 2

Synthesis of ds-cDNA, sense ss-cDNA, and PCR amplification of the jun oncogene-specific ds-cDNA from human leukocytes.

(I) Polydeoxyribonucleotide-immobilized microtiter plate. Polydeoxyribonucleotide-immobilized microliter plates were prepared as described in Example 1 paragraph (2).

(II) Preparation of cell lysates from human leukocytes. Three mls of heparinized blood were diluted three fold with phosphate buffered saline (PBS), and overlayered onto 3 mls IsoLymph (Gallard-Schlesinger) in a 15 ml tube. After centrifugation at 400×g for 30 minutes, cells in the intermediate layer between IsoLymph and plasma were collected into a fresh tube, and washed three times with PBS. 150 μl of lysis buffer was added to the cellular pellet, and cells were completely lysed by repeated passage through an 18G needle. Cell lysates were then incubated at 45° C. for 30 minutes with intermittent shaking to reduce RNase activity.

(III) Ds-cDNA synthesis on the microtiter plate. A solution of 5M NaCl was added to the cell lysate prepared in paragraph (II) and adjusted to a final concentration of 0.5M. This solution was then diluted 10,100 and 1000 fold with lysis buffer containing 0.5M NaCl. Fifty μl each diluted sample was added into wells of the polydeoxyribonucleotide-immobilized microtiter plate, and incubated at room temperature for 30 minutes to allow hybridization between the bound poly-(dT) sequence and the poly(A) tail of the isolated cellular mRNA. After hybridization, the lysis buffer was removed, and each well was washed twice with RNA washing buffer. Fifty μl of RT buffer and 500 units of reverse transcriptase were added into each well and incubated at 37° C. for 1 hour to initiate first strand cDNA synthesis. The buffer was then replaced with 50 μl of ds-cDNA synthesis buffer, and the plates were incubated at 16° C. for 3 hours to cause ds-cDNA synthesis.

(IV) Preparation of ss-cDNA from the plates. The ds-cDNA synthesized as described in paragraph (III) was washed with cDNA washing buffer 5 times, and incubated in 50 μl of DEPC-water at 80° C. for 10 minutes to heat denature the compementary DNA strands. Liquid supernatents were then immediately transferred to fresh 0.65-ml tubes, and stored at −20° C.

(V) Synthesis of PCR primers for amplification of jun oncogene specific mRNA. Sense (jun-s) and antisense (jun-as) oligodeoxyribonucleotides specific for jun oncogenes were synthesized in a DNA synthesizer as described in Example 1 paragraph (1). The nucleotide sequences were as follows:

jun-s 5'-CCCTGAAGGAAGAGCCGCAGAC-3' (Seq ID No. 7)
jun-as 5'-CGTGGGTCATGACTTTCTGCTTGAGCTG-3' (Seq ID No. 8)

(VI) PCR amplification of cDNA. To 1 μl of ss-cDNA as described in paragraph (IV), 0.1 μg (1 μl) each of jun-s and jun-as oligonucleotides, 5 μl of 10× PCR buffer (Promega), 1 μl of 25 mM $MgCl_2$, 4 μl of 10 mM dNTP mixture (Promega), 0.5 μl Taq polymerase (Promega), and 36.5 μl of DEPC-water were mixed. Two drops of mineral oil were overlayered onto the reaction mixture to prevent evaporation. The reaction mixture was first heated at 95° C. for 10 minutes, then PCR was carried out in a Thermal cycler (Model 480, Perkin-Elmer Cetus) with 30 cycles of annealing at 55° C. for 1.5 minutes, extension at 72° C. for 4 minutes and denaturing at 95° C. for 1.5 minutes as described in Example 1 paragraph (9).

Ten μl of the resultant PCR products were then mixed with 1 μl of 10× loading buffer, and applied to a 1.5% agarose gel containing 5 μg/ml ethidium bromide. Electrophoresis was carried out in a 1× TBE buffer at 100 V/6.5 cm width for approximately 1 hour. After electrophoresis, fluorescent DNA bands were recorded onto Polaroid film. Samples loaded on the gel included a 1:1000 dilution, full strength (equivalent to 1 ml of blood), 1:10, and 1:100 dilution respectively of the leukocyte lysate. Results indicated that the jun oncogene was amplified from the 1:10 and 1:100 dilution displaying an estimated size of 370 base pairs. This size is similar to the 372 bp theoretical value.

EXAMPLE 3

PCR amplification of the tachykinin receptor-specific ds-cDNA from human leukocytes.

i) Synthesis of PCR primers for amplification of tachykinin receptors-specific mRNA. Sense (tac-s) and antisense (tac-as) oligodeoxyribonucleotides specific for the tachykinin receptor were synthesized using a DNA synthesizer as described in Example 1 paragraph (1). The nucleotide sequences were as follows:

| | |
|---|---|
| tac-s | 5'-GCCAGCATCTACTCCATGAC-3' (Seq ID No. 9) |
| tac-as | 5'-GGGCAGCCACGAGATGG-3' (Seq ID No. 10) | ii) PCR amplification of cDNA. To 1 µl of ss-cDNA from cell lysates as described in Example 2 Paragraph (IV), 0.1 µg (1 µl) each of tac-s and tac-as oligonucleotides, 5 µl of 10× PCR buffer, 1 µl of 25 mM $MgCl_2$, 4 µl of 10 mM dNTP mixture, 0.5 µl Taq polymerase, and 36.5 µl of DEPC-water were mixed. Two drops of mineral oil were overlayered onto the reaction mixture to prevent evaporation. The reaction was first heated to 95° C. for 10 minutes, then PCR was carried out in a Thermal cycler (Model 480, Perkin-Elmer Cetus) with 30 cycles of annealing at between 45° C. and 55° C. for 1.5 minutes, extension at 72° C. for 4 minutes and denaturing at 95° C. for 1.5 minutes as described in Example 1 paragraph (9). Ten µl of PCR products were then mixed with 1 µl of 10× loading buffer, heated to 65° C. for 5 minutes, and applied to a 1.5% agarose gel containing 5 µg/ml ethidium bromide. Electrophoresis was carried out in a 1× TBE buffer at 100 V/6.5 cm width for approximately 1 hour. After electrophoresis, the DNA bands were recorded onto Polaroid film. Results are discussed in Example 4 below.

EXAMPLE 4

PCR amplification of the ornithine decarboxylase (ODC) -specific ds-cDNA from human leukocytes.

a) Synthesis of PCR primers for amplification of ODC-specific mRNA. Sense (OCD-s) and antisense (ODC-as) oligodeoxyribonucleotides specific for ODC were synthesized in a DNA synthesizer as described in Example 1 paragraph (1). The nucleotide sequences were as follows:

| | |
|---|---|
| ODC-s | 5'-GACTCTGGAGTGAGAATCATA-3' (Seq ID No. 11) |
| ODC-as | 5'-ATCCAATCACCCACATGCATT-3' (Seq ID No. 12) | b) PCR amplification of cDNA. To 1 µl of ss-cDNA from cell lysates 0.1 µg (1 µl) each of ODC-s and ODC-as oligonucleotides, 5 µl of 10× PCR buffer, 1 µl of 25 mM $MgCl_2$, 4 µl of 10 mM dNTP mixture, 0.5 µl Taq polymerase, and 36.5 µl of DEPC-water were mixed. Two drops of mineral oil were overlayered onto the reaction mixture to prevent evaporation. The PCR reaction was carried out as described in Example 1 Paragraph (9). Ten µl of the PCR reaction products were then mixed with 1 µl of 10× loading buffer, heated at 65° C. for 5 minutes, and applied to a 1.5% agarose gel containing 5 µg/ml ethidium bromide. Electrophoresis was carried out in a 1× TBE buffer at 100 V/6.5 cm width for approximately 1 hour. After electrophoresis, gels were exposed to UV light in order to fluoresce the DNA bands, and recorded onto Polaroid film.

Results indicated that the gene for ODC was amplified at both annealing temperatures of 45° C. and 55° C. while the genes for the tachykinin receptor and jun oncogenes were only amplified at 45° C.

EXAMPLE 5

Construction of a cDNA library from ds-cDNA synthesized onto the polydeoxyribonucleotide-immobilized microtiter plates, and introduction of the cDNA library into bacteria.

(1) Ligation of the SP6-SalI adaptor to ds-cDNA synthesized on the microtiter plate. Human leukocyte ds-cDNA synthesized on microtiter plates as described in Example 2 paragraph (III) were ligated with SP6-SalI adaptors, and the cDNA was then digested with SalI as described in Example 1 Paragraph (7).

(2) Removal of ds-cDNA from the microtiter plate. After SalI digestion as described above, wells were washed with cDNA washing buffer 3 times, and incubated in 5 µl of H buffer, 44 µl of DEPC-water and 10 units (1 µl) of NotI (Boerhinger-Mannheim) at 37° C. overnight to cleave the NotI site on the immobilized polydeoxyribonucleotide. The reaction mixture was then transferred to a fresh 0.65-ml tube, and heated at 65° C. for 20 minutes to deactivace NotI.

(3) Ligation of ds-cDNA into a vector (cDNA library construction). Ten µl of heat-denatured ds-cDNA as described above was mixed with 4 µl of 5× T4 ligase buffer, DEPC-water, 1 µl (50 ng) of NotI-SalI pre-digested pSPORT vector (Gibco-BRL), 1 µl of T4 ligase, and incubated at room temperature for 3 hours to ligate the cDNA and the vector. In order to precipitate the cDNA-vector complex, 5 µl (5 µg) of yeast tRNA (Gibco-BRL), 12.5 µl of 7.5M ammonium acetate and 70 µl of ethanol was added into the reaction mixture and placed at −70° C. overnight. The DNA was centrifuged at 15,000 rpm for 20 minutes at 4° C. (MTX-150, Tomy), and the pellet was resuspended in 1 ml of 70% ethanol and recentrifuged at 15,000 rpm for 5 minutes at 4° C. After the supernatant was removed, the pellet was dried by a Speed-vac vacuum centrifuge (Savant), and resuspended in DEPC-water.

(4) Transformation. A cDNA-ligated plasmid as described above was resuspended in 5 µl of DEPC water. One 1 µl was then mixed with 25 µl of competent cells (ElectroMax DH10a, Gibco-BRL) on ice and then placed into a 0.1 cm cuvette (BioRad). Electroporation was carried out at 16.6 kV/cm to incorporate plasmids into the cells. One ml of SOC medium was added into the cuvette, and cells were then transferred to a fresh 10-ml polypropylene tube. The cell mixture was incubated at 37° C. for exactly 1 hour with constant shaking at 225 rpm. After cells were diluted 10 and 100 fold with SOC medium, 50 µl were spread onto Liquid Broth agar plates containing 100 µg/ml ampicillin and incubated at 37° C. overnight. The number of colonies was then manually counted.

As shown in Table I, approximately 600,000–900,000 colonies were obtained from each well, representing 1 ml of blood leukocytes.

TABLE I

| Experiment Number | Number of Colonies* |
| --- | --- |
| 1 | 900,000 |
| 2 | 850,000 |
| 3 | 600,000 |

*: number of colonies from 1 ml of blood leukocytes.

This experiment shows that ds-cDNA can be amplified and subsequently cloned into a plasmid vector. This method is advantageously both efficient and fast.

Thus, the foregoing examples demonstrate the wide-ranging utility of the present invention. However, as these examples are intended to illustrate, rather than to limit the present invention, the scope of the present invention is to be interpretted with reference to the appended claims.

We claim:

1. A method of making sense ss-cDNA, said method comprising:

(a) binding a polynucleotide covalently by its 5' end to a well of a microtiter plate, said polynucleotide being complementary to a polyadenylic acid tail of mRNA, thereby creating a polynucleotide-linked microtiter plate;

(b) adding a sample solution containing mRNA with a polyadenylic acid tail to said well of said polynucleotide-linked microtiter plate;

(c) incubating said sample solution in contact with said well of said polynucleotide-linked microtiter plate, thereby permitting the polyadenylic acid tail of said mRNA to hybridize with said sequence complementary to a polyadenylic acid tail of mRNA, and thereby producing a first liquid phase and a first solid phase;

(d) synthesizing an antisense cDNA complementary to said mRNA, using said mRNA as a template and reverse transcriptase to mediate enzymatic synthesis of said antisense cDNA in the presence of dATP, dCTP, dGTP, and dTTP;

(e) synthesizing a first sense cDNA complementary to said antisense cDNA, by adding RNAse H, DNA ligase, and DNA polymerase to mediate enzymatic synthesis of said first sense cDNA in the presence of dATP, dCTP, dGTP, and dTTP, thereby producing a ds-cDNA linked to said well of said polynucleotide-linked microtiter plate as a second solid phase in a second liquid phase;

(f) discarding said second liquid phase;

(g) adding liquid to said second solid phase;

(h) heat-denaturing said ds-cDNA, thereby producing a third liquid phase containing said first sense ss-cDNA, and a third solid phase containing said antisense cDNA;

(i) removing said third liquid phase to obtain said first sense ss-cDNA;

(j) synthesizing a second sense cDNA complementary to said antisense cDNA, by adding DNA ligase, and DNA polymerase to mediate enzymatic synthesis of said second sense cDNA in the presence of dATP, dCTP, dGTP, and dTTP, thereby producing a ds-cDNA linked to said well of said polynucleotide-linked microtiter plate as a fourth solid phase in a fourth liquid phase;

(k) discarding said fourth liquid phase;

(l) adding liquid to said fourth solid phase;

(m) heat-denaturing said ds-cDNA, thereby producing a fifth liquid phase containing said second sense ss-cDNA, and a fifth solid phase containing said antisense cDNA; and (n) removing said fifth liquid phase to obtain said second sense ss-cDNA.

2. The method of claim 1 wherein the solid phase is stored in a stock solution or in a dry state between steps (i) and (j), or following step (n).

3. The method of claim 1 further comprising step (o), wherein step (o) comprises repeating steps (j) through (n) one or more times to obtain additional cDNAs complementary to said antisense cDNA linked to said well of said polynucleotide-linked microtiter plate.

4. The method of claim 3 wherein the solid phase is stored in a stock solution or in a dry state between steps (i) and (j), between steps (n) and (o), or between each time steps (j) through (n) are repeated.

* * * * *

UNITED STATES PATENT AND TRADEMARK OFFICE
Certificate

Patent No. 5,656,462                                                                           Patented: August 12, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Masato Mitsuhashi, Irvine, CA; and Tatsuo Akitaya, Irvine, CA.

Signed and Sealed this Sixth Day of July 2004.

JOHN L. LEGUYADER
*Supervisory Patent Examiner*
Art Unit 1600

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: T7 Promoter Sequence ( x i ) SEQUENCE DESCRIPTION: SEQ ID NO:1:

AATACGACTC ACTATAG                      17

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: SP6 PROMOTER SEQUENCE ( x i ) SEQUENCE DESCRIPTION: SEQ ID NO:2:

CATTTAGGTG ACACTATAGA A               21

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( A ) ORGANISM: SALI-SP6 ADAPTER SEQUENCE ( x i ) SEQUENCE DESCRIPTION: SEQ ID NO:3:

TCGACATTTA GGTGACACTA TAGAA    25

( 2 ) INFORMATION FOR SEQ ID NO:4:

( i ) SEQUENCE CHARACTERISTICS:
        ( A ) LENGTH: 53 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: 53-MER OLIGO CONTAINING ECOR1, NOTI, AND T7
            PROMOTER ( x i ) SEQUENCE DESCRIPTION: SEQ ID NO:4:

AGCTGAATTC GCGGCCGCAA TACGACTCAC TATAGTTTTT TTTTTTTTT TTT    53

( 2 ) INFORMATION FOR SEQ ID NO:5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: G2-S OLIGONUCLEOTIDE PRIMER ( x i ) SEQUENCE DESCRIPTION: SEQ ID NO:5:

AGCACCATTG TGAAGCAGAT GA    22

( 2 ) INFORMATION FOR SEQ ID NO:6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: G2-AS OLIGONUCLEOTIDE PRIMER ( x i ) SEQUENCE DESCRIPTION: SEQ ID NO:6:

CTCTGGCCTC CCACATCAAA CA    22

( 2 ) INFORMATION FOR SEQ ID NO:7:

( i ) SEQUENCE CHARACTERISTICS:
    ( A ) LENGTH: 22 base pairs
    ( B ) TYPE: nucleic acid
    ( C ) STRANDEDNESS: single
    ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
    ( A ) ORGANISM: JUN-S OLIGONUCLEOTIDE PRIMER ( x i ) SEQUENCE DESCRIPTION: SEQ ID NO:7:

CCCTGAAGGA AGAGCCGCAG AC    22

( 2 ) INFORMATION FOR SEQ ID NO:8:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: JUN-AS OLIGONUCLEOTIDE PRIMER ( x i ) SEQUENCE DESCRIPTION: SEQ ID NO:8:

CGTGGGTCAT GACTTTCTGC TTGAGCTG    28

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: TAC-S OLIGONUCLEOTIDE PRIMER ( x i ) SEQUENCE DESCRIPTION: SEQ ID NO:9:

GCCAGCATCT ACTCCATGAC    20

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: TAC-AS OLIGONUCLEOTIDE PRIMER ( x i ) SEQUENCE DESCRIPTION: SEQ ID NO:10:

GGGCAGCCAC GAGATGG 17

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: ODC-S OLIGONUCLEOTIDE PRIMER ( x i ) SEQUENCE DESCRIPTION: SEQ ID NO:11:

GACTCTGGAG TGAGAATCAT A 21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: ODC-AS OLIGONUCLEOTIDE PRIMER ( x i ) SEQUENCE DESCRIPTION: SEQ ID NO:12:

ATCCAATCAC CCACATGCAT T 21